(12) United States Patent
Abed

(10) Patent No.: US 9,074,183 B2
(45) Date of Patent: Jul. 7, 2015

(54) METHOD AND APPARATUS FOR REGULATING OPTIMUM FLOW OF SEMEN AND SEPARATING MOTILE SPERMS

(76) Inventor: Farhang Abed, Tehran (IR)

( * ) Notice: Subject to any disclaimer, the term of this patent is extended or adjusted under 35 U.S.C. 154(b) by 1773 days.

(21) Appl. No.: 12/039,776

(22) Filed: Feb. 29, 2008

(65) Prior Publication Data

US 2008/0311653 A1    Dec. 18, 2008

(30) Foreign Application Priority Data

Mar. 14, 2007  (GB) .................................. 0704875.4

(51) Int. Cl.
*C12M 1/00*  (2006.01)
*C12N 5/071*  (2010.01)
*A61K 35/12*  (2015.01)

(52) U.S. Cl.
CPC .............. *C12N 5/0612* (2013.01); *A61K 35/12* (2013.01)

(58) Field of Classification Search
CPC ...... C12M 27/02; C12M 35/04; C12M 21/04; C12M 23/14; C12M 29/10; C12M 21/06; C12N 5/0612; A61K 38/00; A61K 48/00; A61K 35/12; C07K 2319/00; A01K 2217/05; A61B 17/435; A01N 1/02; A01N 1/0263; A61D 19/04
USPC ....................... 435/173.9, 283.1, 325; 600/33
See application file for complete search history.

(56) References Cited

U.S. PATENT DOCUMENTS

| | | | |
|---|---|---|---|
| 4,413,059 A * | 11/1983 | Tihon et al. ................. | 435/283.1 |
| 2005/0079480 A1 * | 4/2005 | Loskutoff ......................... | 435/2 |
| 2006/0088930 A1 * | 4/2006 | Smith et al. ................ | 435/287.9 |

OTHER PUBLICATIONS

Whatman. "Cyclopore Polycarbonate and Polyester Membranes". (www.whatman.com/products.aspx?PID=10) (copyright 2007-2009). printed Aug. 29, 2011.*

* cited by examiner

*Primary Examiner* — Michael Hobbs
(74) *Attorney, Agent, or Firm* — Barry Choobin; Patent 360

(57) ABSTRACT

The present invention discloses method and apparatus for regulating optimum flow of semen and separating motile sperms. The device consists of; a first cylindrical shape container, comprising a first external diameter, second external diameter, a thirds external diameter and a mesh, wherein said mesh is comprised of plurality of pores and attached to lower bottom of said first cylindrical shape container; a second cylindrical shape container comprising an internal diameter and an external diameter, wherein said second cylindrical shape container is closed ended at bottom, and embraces said first cylindrical shape container at said second external diameter of said first cylindrical shape container, thereby creating at least a first predetermined distance and at least a second predetermined distance, wherein said at least a first predetermined distance regulates air coming from said second cylindrical shape container, thereby regulating flow of semen and separating motile sperms coming through said mesh to said second cylindrical shape container.

2 Claims, 2 Drawing Sheets

METHOD AND APPARATUS FOR REGULATING OPTIMUM FLOW OF SEMEN AND SEPARATING MOTILE SPERMS

SPONSORSHIP STATEMENT

The present invention is sponsord by Iranian National Science foundation for international filing (INSF).

FIELD OF THE INVENTION

The present invention relates generally to infertility, and more particularly to an apparatus and method for regulating optimum flow of semen and separating motile sperms thereby preparing sperms for Assisted Reproductive Technology (ART), IVF (In Vitro Fertilization), GIFT (Gamete Intra-Fallopian Transfer), ICSI (Intra Cytoplasmic Sperm Insertion), and IUI (Intra Uterine Insemination).

BACKGROUND OF THE INVENTION

To increase the chance of fertilization, several kinds of treatment including IUI, IVF, GIFT and ICSI are performed with sperm preparations composed of viable and motile sperms, free of seminal plasma and debris.

Under in vivo conditions, potentially fertile spermatozoa are separated from immotile spermatozoa, debris and seminal plasma in the female genital tract by active migration through the cervical mucus. During this process, not only progressively motile spermatozoa are selected, but male germ cells also undergo physiological changes called capcitation, which are fundamental prerequisites for the sperm's functional competence with regard to acrosome reaction. The introduction of assisted reproduction, especially of IVF, during the 1980's, led to the development of a wide range of different sperms separation methods. Following the development of the classical swim-up method by Mahadevan & Baker, more complicated techniques were developed to increase the number of motile spermatozoa even in severe anthological cases. On principle, these techniques can be differentiated in migration, density gradient centrifugation and filtration techniques. For all migration methods, the self-propelled movement of spermatozoa is an essential prerequisite, while for density gradient centrifugation and filtration techniques the methodology is based on a combination of the sperm cells' motility and their retention at phase borders and adherence to filtration matrices, respectively. The migration techniques can again be subdivided into swim-up, under-lay and migration-sedimentation methods. For density gradient centrifugation, separation media like Ficoll®, Nycodenz and Percoll® including the products (lxaPrep®, PureSperm®, Isolate®. SilSelect®) have recently been introduced to replace Percoll®. The filtration methods like glass wool filtration and filtration of spermatozoa on Sephadex beads and membranes are alternative techniques.

At present time, there is no ideal method for preparation of sperms for ART. The ideal sperms separation technique should (i) be quick, easy and cost-effective, (ii) isolate as much motile spermatozoa as possible, (iii) not cause sperm damage or non physiological alterations of the separated sperm cells, (iv) eliminate dead spermatozoa and other cells, including leukocytes and bacteria, (v) eliminate toxic or bioactive substances like decapacitation factors or reactive oxygen species (ROS), and (vi) allow processing of larger volumes of ejaculates. Since none of the methods available meets all these requirements, a variety of sperms separation techniques are mandatory in clinical practice to obtain an optimal yield of functionally competent spermatozoa for insemination purposes. Depending on the ejaculate quality, these methods have different efficiency and areas of use. In the conventional swim-up technique, functional spermatozoa can come into close cell-to-cell contact with defective sperm or leukocytes by centrifugation, thus causing massive oxidative damages of the sperm plasma membrane by ROS and consequently of sperm functions, therefore, the quality of the ejaculates has direct consequences on the choice of a sperm separation method.

Also Aitken and Clarkson have shown that centrifugal force generates the production of reactive oxygen species that may damage sperm and impair their fertility potential.

It has been reported that when sperms are put into a fluid flow, the motile sperms rapidly align themselves and swim upstream. Non-motile and sluggish sperms, along with other cellular components, are washed downstream away from the motile sperms. Cilia have been shown to be present in the endometrial cells of many mammals. Ciliary's currents in both the fallopian tubes and the uterus move in the same direction and extend towards the external os. One may expect that this flow act as a guide for sperms, leading sperm with the correct motility parameters towards the site of fertilization at the ampoule of the fallopian tubes. Secondly, this flow acts as a natural selection mechanism to optimize the quality of sperm able to reach the fertilization site.

Based on this phenomenon of the sperms the present invention has a number of advantages over conventional methods of preparing sperms and it seems that has all of the characteristics of an ideal method including but not limited to;

Not inducing any damage to the sperms, because the procedure does not require any use of chemicals or centrifuges.

Rapid and simple preparation process.

Physicians can use the module without the need for expensive laboratory equipment.

The use of the module in accordance with the invention not only serves to separate sperms, but also washes the sperms, thus eliminating the need for any centrifuge process.

The present invention can be used not only for the separation of motile from non-motile sperms but can also be used with motile, morphologically normal sperms, to provide sperms suitable for ART and IUI procedures.

SUMMARY OF THE INVENTION

An embodiment of the present invention, is a device for regulating optimum flow of semen and separating motile sperms, wherein said device consists of; a first cylindrical shaped container, wherein said first cylindrical shaped container comprises a first external diameter, second external diameter, a third external diameter and a mesh, wherein said mesh is comprised of plurality of pores and attached to lower bottom of said first cylindrical shaped container;

a second cylindrical shaped container wherein said second cylindrical shaped container comprises an internal diameter and an external diameter, wherein said second cylindrical shaped container has closed end at bottom, and embraces said first cylindrical shaped container at said second external diameter of said first cylindrical shaped container, thereby creating at least a first predetermined distance and at least a second predetermined distance, wherein said at least a first predetermined distance is the distance between said second external diameter of said first cylindrical shaped container and said internal diameter of said second cylindrical shaped container, and said at least a second predetermined distance is the distance between said third external diameter of said first cylindrical shaped container and said internal diameter of said second cylindrical shaped container, wherein said at least a first predetermined distance regulates air coming from said second cylindrical shaped container, thereby regulating flow of semen and separating motile sperms coming through said mesh to said second cylindrical shaped container.

Yet another embodiment of the present invention is a device wherein said mesh comprises of plurality of pores wherein dimensions of said pores are 10-150 micrometers.

Yet another embodiment of the present invention is a device wherein dimensions of said pores are 50 micrometers.

Yet another embodiment is a device wherein said device regulates optimum flow of semen and separates motile sperms based on said at least a first predetermined distance or said dimensions of said poses or combination thereof.

Yet another embodiment of the present invention is a method for regulating optimum flow of semen and separating motile sperms, wherein said method consists of:

preparing a first cylindrical shaped container, wherein said first cylindrical shaped container comprises a first external diameter, a second external diameter, a third external diameter and a mesh, wherein said mesh is comprised of plurality of pores and attached to lower bottom of said first cylindrical shaped container;

preparing a second cylindrical shaped container wherein said second cylindrical shaped container comprises an internal diameter and an external diameter, wherein said second cylindrical shaped container has closed end at bottom;

embracing said first cylindrical shaped container at said second external diameter of said first cylindrical shaped container;

creating at least a first predetermined distance and at least a second predetermined distance, wherein said at least a first predetermined distance is the distance between said second external diameter of said first cylindrical shaped container and said internal diameter of said second cylindrical shaped container, and said at least a second predetermined distance is the distance between said third external diameter of said first cylindrical shaped container and said internal diameter of said second cylindrical shaped container;

placing semen in said first cylindrical shaped container;

adding a layer of predetermined amount of media to said semen;

regulating air coming from said second cylindrical shaped container based on said at least a first predetermined distance, thereby regulating flow of semen and separating motile sperms coming through said first cylindrical shaped container to said second cylindrical shaped container.

BRIEF DESCRIPTION OF THE DRAWINGS

The present invention is further described hereinafter with reference to one of its preferred embodiments shown in the accompanying drawings, in which.

DETAILED DESCRIPTION

Figure 1:
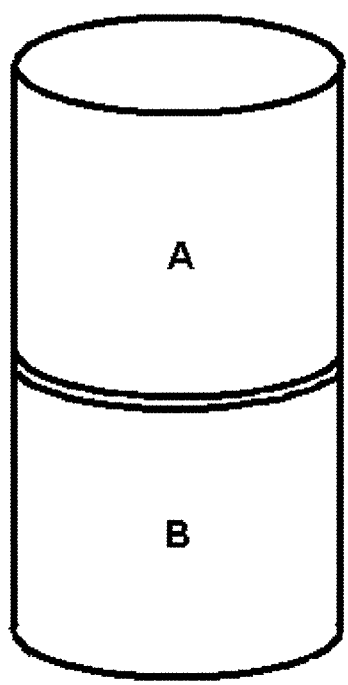
FIG. 1 is a side view of the tubes when assembled together.
Figure 2:
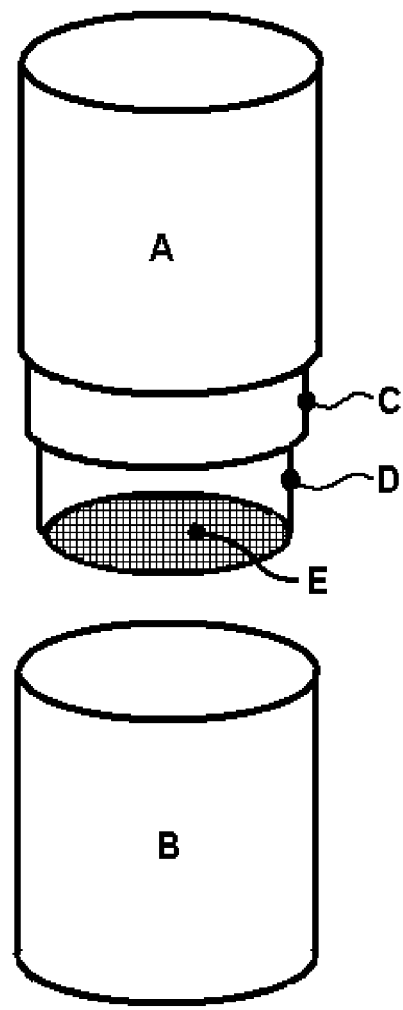
FIG. 2 is a perspective view of tubes according to FIG. 1.

With attention to the embodiment of FIGS. 1 & 2 the present invented device involves two disposable plastic tubes A & B (FIG. 1), which are assembled together. Two ends of the upper tube A are open (FIG. 2), and the external wall of the lower part C & D becomes narrow and narrower in distinct steps in order to enter it in the lower tubes B and use it (FIG. 2, C&D).

The lower tube B is a plastic cylinder, whose upper end is completely open, and its lower end is closed (FIG. 2, B).

There is a mesh E at the lower end of the upper tube A, which is attached to the lower end of the tube, completely (FIG. 2, E). This mesh can be made of paper, plastic, glass fibers and even metals.

The narrow parts C & D of the upper tube A is put in the lower tube B and assembled together.

Because the external diameter of the narrow part of the upper tube A is less than internal diameter of the lower tube B slightly, when these tubes A & B are assembled together some fine passage is formed between the narrow part of the external wall of the upper tube A and the internal wall of the lower tube B. The differences between diameters of the external wall narrow part of the upper tube A and the internal wall of the lower tube B are complement of the dimension of mesh pores so that they regulate the optimum flow rate of semen.

First, some semen is placed on floor of the upper tube A just on the mesh E, via using a Pasteur pipette or syringe, and then some media like Ham's F-10 is gently placed on the upper semen.

Then, the tube is put in an incubator or on a warmer. During the procedure, semen flows from upper tube A, because of the gravity and drops in lower tube B via mesh pores.

The air-which is in lower tube-exists, simultaneously, via the fine passage which is the result of the distance between walls of the upper and the lower tubes A & B.

When semen flows in mesh pores, all of the non motile sperms, cells, debris and also seminal plasma enter the lower tube B, while active motile sperms separate by swimming to upstream and go to the upper part of the upper tube A, which is the place of medium.

Finally, all of the semen flows from the upper tube A to the lower one B, and merely the media remains, which contains active motile and normal sperms.

Then, this media, which contains active sperms, aspirated via syringe or Pasteur pipette and used for ART or IUI procedures.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A device for regulating optimum flow of semen and separating motile sperms, wherein said device comprising:

a first cylindrical shaped container, wherein said first cylindrical shaped container comprises a first external diameter, a second external diameter, a third external diameter and a mesh, wherein said mesh is comprised of plurality of pores and attached to lower bottom of said first cylindrical shaped container; wherein said mesh comprises of plurality of pores wherein dimensions of said pores are 10-150 micrometers, and wherein said mesh is made of at least one of paper, plastic, glass fibres and metals, wherein said first cylindrical shaped container includes an upper open end and a lower open end, and wherein external diameter of external wall of said first cylinder shaped container becomes narrow in distinct steps;

a second cylindrical shaped container wherein said second cylindrical shaped container comprises an internal diameter and an external diameter, wherein said second cylindrical shaped container is closed ended at bottom, and embraces said first cylindrical shape container at said second external diameter of said first cylindrical shaped container, thereby creating at least a first predetermined distance and at least a second predetermined distance, wherein the second cylindrical shaped container includes an upper open end and lower closed end;

wherein said at least a first predetermined distance is the distance between said second external diameter of said first cylindrical shaped container and said internal diameter of said second cylindrical shaped container, and said at least a second predetermined distance is the distance between said third external diameter of said first cylindrical shaped container and said internal diameter of said second cylindrical shaped container, wherein the first external diameter of the first cylindrical shaped container is less than the internal diameter of the second cylindrical shaped container, wherein a difference between diameters of said narrow part of the external wall of said first cylindrical shaped container and said internal wall of the second cylinder shaped container are complement of the mesh pores such that said at least a first predetermined distance regulates an air coming from said second cylindrical shape container, thereby regulating a flow of semen and separating motile sperms coming through said mesh to said second cylindrical shaped container;

wherein the semen flows from the first cylinder shaped container and drops in the second cylinder shaped container via mesh pores by gravity and air which is in the second cylinder shaped container exit simultaneously via a fine passage which is the result of the distance between walls of the first cylinder shaped container and the second cylinder shaped container;

wherein said mesh provided on said first cylinder shaped container is attached to the lower end of said first cylinder shaped container completely, such that the semen flows from the first cylinder shaped container to the second lower shaped container via the mesh pores such that all non motile sperms, cells, debris and seminal plasma enter the second cylinder shaped container and active motile sperms separate by swimming to upstream and go to an upper part of the first cylinder shaped container.

2. The device as claimed in claim 1, wherein said device regulates optimum flow of semen and separates motile sperms based on said at least first predetermined distance or said dimensions of said pores or combination thereof, wherein a difference between diameters of external wall of the narrow part of the first cylindrical shaped container and the internal wall of the second cylinder shaped container are complement of the dimensions of the mesh pores so that they regulate the optimum flow rate of semen.

* * * * *